(12) United States Patent
Iseri et al.

(10) Patent No.: US 8,988,228 B2
(45) Date of Patent: Mar. 24, 2015

(54) ELECTRONIC MODULE FOR TRACKING HAND HYGIENE

(71) Applicants: Mert Iseri, Evanston, IL (US); Yuri Malina, Evanston, IL (US); Jori Hardman, Chicago, IL (US)

(72) Inventors: Mert Iseri, Evanston, IL (US); Yuri Malina, Evanston, IL (US); Jori Hardman, Chicago, IL (US)

(73) Assignee: Swipesense, Inc., Evanston, IL (US)

( * ) Notice: Subject to any disclaimer, the term of this patent is extended or adjusted under 35 U.S.C. 154(b) by 62 days.

(21) Appl. No.: 13/769,180

(22) Filed: Feb. 15, 2013

(65) Prior Publication Data

US 2013/0257615 A1 Oct. 3, 2013

Related U.S. Application Data

(60) Provisional application No. 61/619,815, filed on Apr. 3, 2012, provisional application No. 61/659,006, filed on Jun. 13, 2012.

(51) Int. Cl.
*G08B 23/00* (2006.01)
*G08B 21/18* (2006.01)
*G08B 21/24* (2006.01)
*G06F 19/00* (2011.01)

(52) U.S. Cl.
CPC ............. *G08B 21/18* (2013.01); *G08B 21/245* (2013.01); *G06F 19/327* (2013.01)
USPC ..................... 340/573.1; 340/540; 340/573.6; 340/603

(58) Field of Classification Search
None
See application file for complete search history.

(56) References Cited

U.S. PATENT DOCUMENTS

| | | | |
|---|---|---|---|
| 3,926,347 A | 12/1975 | Low et al. | |
| 4,561,571 A | 12/1985 | Chen | 222/207 |
| 4,621,749 A | 11/1986 | Kanfer | 222/153.01 |
| 4,932,562 A | 6/1990 | Christine | |
| 5,421,489 A | 6/1995 | Holzner et al. | 222/207 |
| 6,068,162 A | 5/2000 | De Winter et al. | 222/181.3 |
| 6,152,330 A | 11/2000 | Polan | 222/156 |
| 6,216,916 B1 | 4/2001 | Maddox et al. | 222/105 |
| 6,392,546 B1 | 5/2002 | Smith | |
| 6,619,512 B1 | 9/2003 | Sayers et al. | 222/207 |
| 6,883,563 B2 | 4/2005 | Smith | |
| 7,278,554 B2 | 10/2007 | Armstrong | 922/325 |
| 7,293,645 B2 | 11/2007 | Harper et al. | |

(Continued)

FOREIGN PATENT DOCUMENTS

| | | | |
|---|---|---|---|
| JP | 2010205192 | 9/2010 | G06Q 50/22 |
| KR | 20-0192348 | 8/2000 | A47K 5/12 |

(Continued)

OTHER PUBLICATIONS

Non-Final Office Action dated May 2, 2014 from U.S. Appl. No. 13/769,171 filed Feb. 15, 2013, 15 Pages.

(Continued)

*Primary Examiner* — Travis Hunnings
(74) *Attorney, Agent, or Firm* — Baker Botts L.L.P.

(57) ABSTRACT

In accordance with some embodiments of the present disclosure, an electronic module may comprise a sensor configured to detect a dispensing action, a processor configured to record a dispense indicator when the sensor detects a dispensing action and read a user identifier from a user identifier memory configured to interchangeably operate in conjunction with a plurality of sanitizer dispensers, and a transceiver configured to transmit the user identifier to a network and transmit the dispense indicator to the network.

16 Claims, 9 Drawing Sheets

(56) References Cited

U.S. PATENT DOCUMENTS

| | | | |
|---|---|---|---|
| 7,708,164 B2 | 5/2010 | Pritchard | 222/81 |
| 7,782,214 B1 | 8/2010 | Lynn | |
| 7,789,269 B2 | 9/2010 | Pritchard | 222/81 |
| 7,806,301 B1 | 10/2010 | Ciavarella et al. | 222/207 |
| 7,815,075 B2 | 10/2010 | Simkins | |
| 7,828,176 B2 | 11/2010 | Harper | |
| 7,893,842 B2 | 2/2011 | Deutsch | |
| 7,988,020 B2 | 8/2011 | Shoham et al. | |
| 8,237,558 B2 | 8/2012 | Seyed Momen et al. | |
| 8,360,287 B2 | 1/2013 | Ciavarella et al. | 222/372 |
| 8,640,926 B2 | 2/2014 | McNulty et al. | 222/181.3 |
| 2007/0051752 A1 | 3/2007 | Lapins | |
| 2009/0317270 A1 | 12/2009 | Reynolds | |
| 2010/0094581 A1* | 4/2010 | Cagle | 702/127 |
| 2010/0102085 A1 | 4/2010 | Kanfer et al. | |
| 2010/0117836 A1* | 5/2010 | Seyed Momen et al. | 340/573.1 |
| 2010/0134296 A1 | 6/2010 | Hwang | |
| 2010/0188228 A1 | 7/2010 | Hyland | |
| 2010/0238021 A1 | 9/2010 | Harris | |
| 2010/0332022 A1 | 12/2010 | Wegelin et al. | |
| 2011/0068930 A1* | 3/2011 | Wildman et al. | 340/573.1 |
| 2011/0169646 A1* | 7/2011 | Raichman | 340/573.1 |
| 2012/0112883 A1 | 5/2012 | Wallace et al. | |
| 2012/0118915 A1 | 5/2012 | Harper | |
| 2012/0138637 A1 | 6/2012 | Ciavarella et al. | |
| 2012/0212582 A1 | 8/2012 | Deutsch | |
| 2012/0256741 A1 | 10/2012 | Ophardt | |
| 2013/0257615 A1 | 10/2013 | Iseri et al. | 340/540 |

FOREIGN PATENT DOCUMENTS

| | | | |
|---|---|---|---|
| KR | 20-0192348 Y1 | 8/2000 | |
| KR | 2010-0080744 | 7/2010 | A61L 2/16 |

OTHER PUBLICATIONS

International Search Report and Written Opinion; PCT/US2013/034811; pp. 15.

International Search Report and Written Opinion; PCTUS2013/034815; pp. 13.

International Preliminary Report for Application No. PCT/US2013/034811 mailed Oct. 16, 2014, 11 pages.

International Preliminary Report for Application No. PCT/US2013/034812 mailed Oct. 16, 2014, 6 pages.

International Preliminary Report for Application No. PCT/US2013/034815 mailed Oct. 16, 2014, 10 pages.

\* cited by examiner

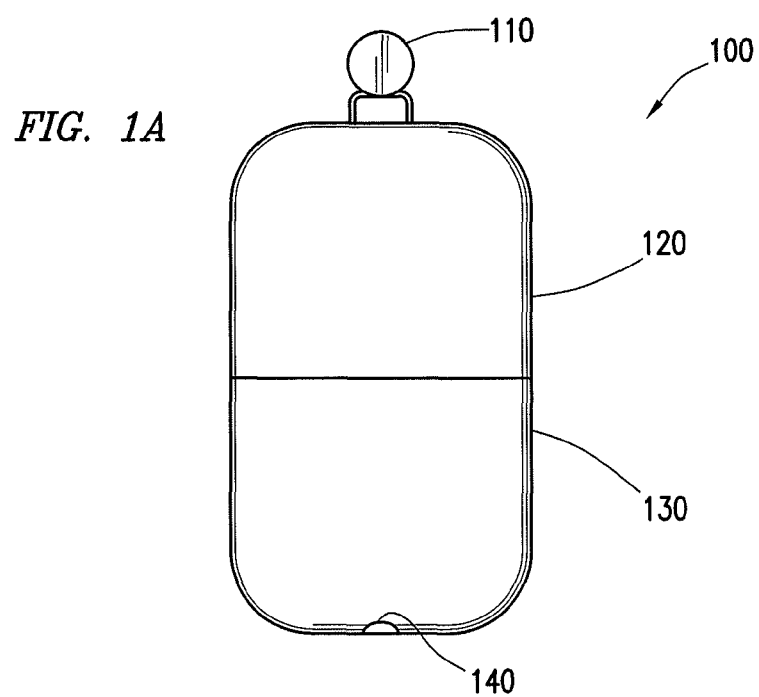
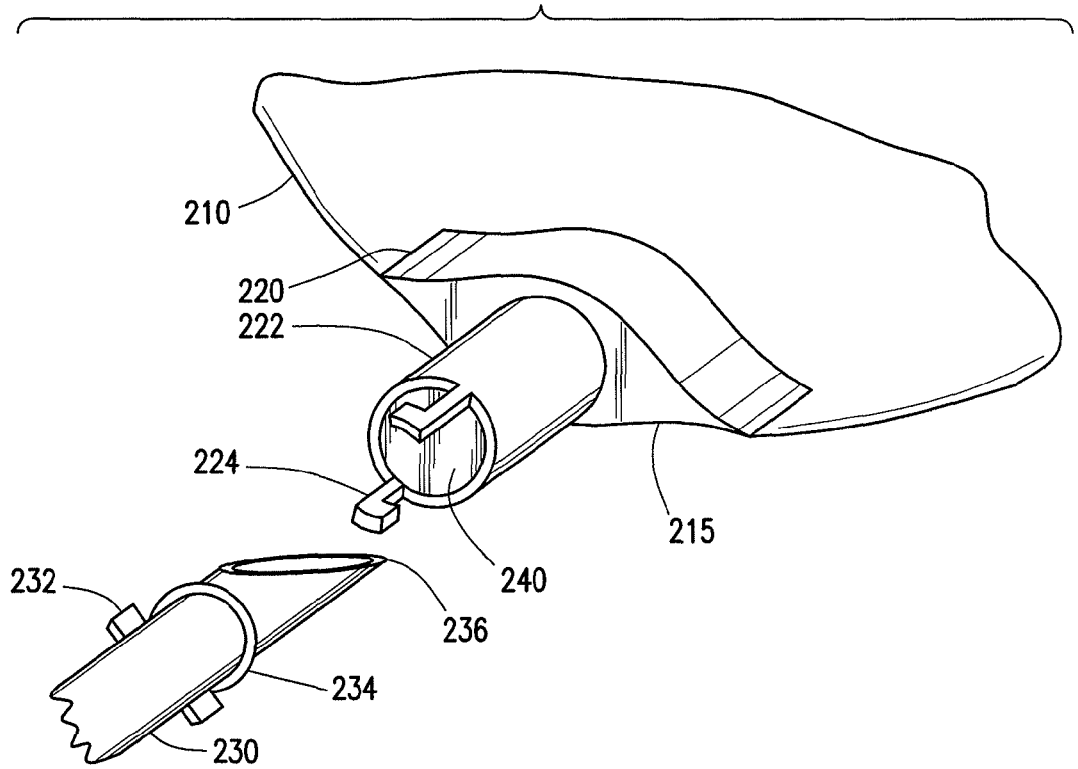

ELECTRONIC MODULE FOR TRACKING HAND HYGIENE

RELATED APPLICATIONS

This application claims the benefit of U.S. Provisional patent application Ser. No. 61/619,815 filed Apr. 3, 2012, the contents of which is incorporated by reference in its entirety.

This application claims the benefit of U.S. Provisional patent application Ser. No. 61/659,006 filed Jun. 13, 2012, the contents of which is incorporated by reference in its entirety.

TECHNICAL FIELD

The present disclosure relates generally to hand hygiene and more particularly to an electronic module for tracking hand hygiene.

BACKGROUND

Hand hygiene is critical to preventing the spread of infection, germs, and/or disease. The prevention of such spreading is especially critical in the hospital environment. Many hospitals and other health care facilities have implemented hand sanitization protocols under which hospital and other health care employees are required to wash or sanitize their hands at regular intervals or during certain actions such as entering a patient's room. In order to maintain compliance with such protocols, hospital employees and other health care workers must have convenient access to hand sanitizers. Moreover, to ensure a sanitary environment, hospitals and other health care facilities may wish to track hand hygiene compliance.

SUMMARY

In accordance with teachings of the present disclosure, disadvantages and problems associated with sanitizer dispensers have been substantially reduced or eliminated.

In one embodiment of the present disclosure, an electronic module is disclosed. The electronic module may comprise a sensor configured to detect a dispensing action, a processor configured to record a dispense indicator when the sensor detects a dispensing action and read a user identifier from a user identifier memory configured to interchangeably operate in conjunction with a plurality of sanitizer dispensers, and a transceiver configured to transmit the user identifier to a network and transmit the dispense indicator to the network.

The object and advantages of the invention will be realized and attained by means of at least the features, elements, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 1A illustrates a hand sanitizer dispenser, in accordance with certain embodiments of the present disclosure;

FIG. 3A illustrates a coupling mechanism for a hand sanitizer dispenser and a pouch, in accordance with certain embodiments of the present disclosure;

DETAILED DESCRIPTION

Figure 1B:
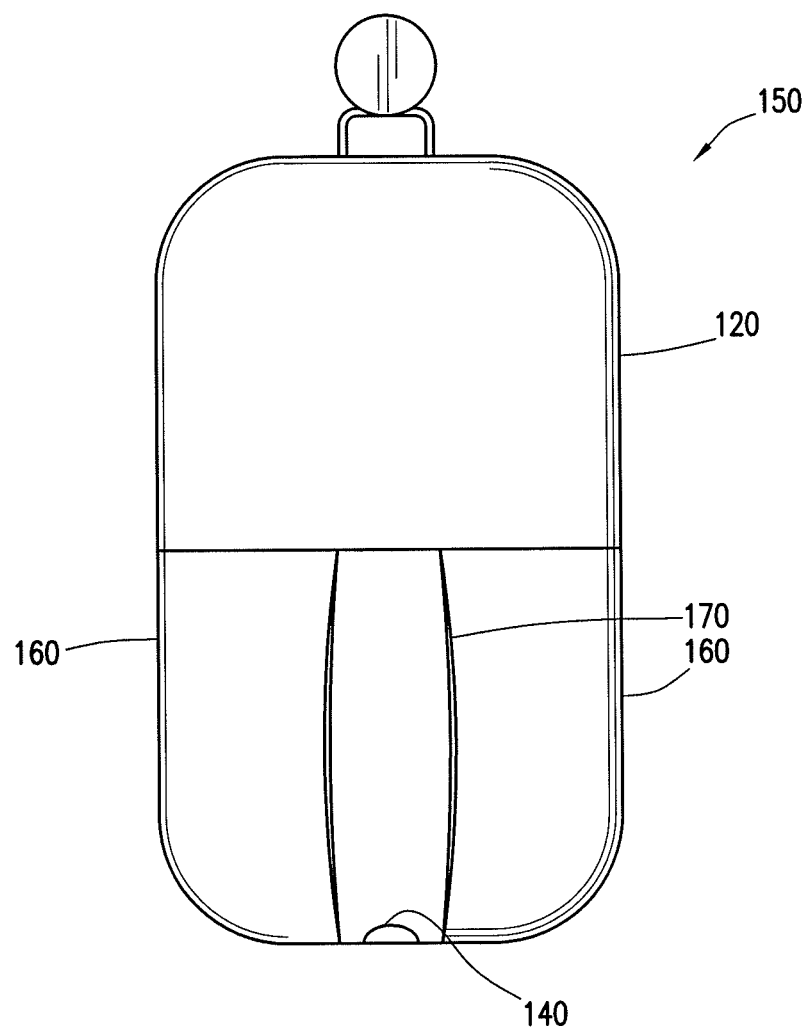
FIG. 1B illustrates a hand sanitizer dispenser, in accordance with certain embodiments of the present disclosure.

In accordance with the teachings of the present disclosure, a method and system for dispensing a hand sanitizer is provided.

FIG. 1A illustrates a hand sanitizer dispenser 100, in accordance with certain embodiments of the present disclosure. Dispenser 100 may include a clip 110, a sanitizer encasement 120, a push plate 130, and a dispenser opening 140. Dispenser 100 may be configured to dispense doses of hand sanitizer that may be in a gel or fluid form. The volume of the dose for each dispensing action may depend on the fraction of the active ingredient in a given sanitizer (e.g., the alcohol content of a given sanitizer), and the amount of the active ingredient that is required for an effective hand cleansing. An effective dose for typical gel sanitizers may range, for example, from 0.75 mL to 1.50 mL. In some embodiments, the hand sanitizer may include an antibacterial active ingredient. For example, dispenser 100 may be configured to dispense doses of alcohol-based sanitizers and/or other types of sanitizers, including but not limited to sanitizers having isopropanol, ethanol, n-propanol, and/or povidone-iodine as the active ingredient. Accordingly, dispenser 100 may be used by any user who may desire to sanitize their hands such as, for example, doctors, nurses, and/or other hospital employees.

Clip 110 may include a suspender clip that may be used to attach dispenser 100 to the clothing of a user. Accordingly, dispenser 100 may be worn by a user such as a hospital employee, and hand sanitizer may be conveniently available to that user regardless of their location within the hospital. For example, clip 110 may be used to attach dispenser 100 to a doctor's or a nurse's scrubs. Though clip 110 is illustrated in FIG. 1A as being coupled to the top of dispenser 100, clip 110 may be coupled to dispenser 100 at any suitable location. Moreover, dispenser 100 may be configured to be attached to a user or a user's clothing by any other suitable attachment techniques, including but not limited to, straps, velcro, magnets, an alligator clip, a lanyard clip, a belt clip, and/or any other suitable types of other clips. In some embodiments, dispenser 100 may include an interchangeable attachment device. For example, clip 110 may be configured to be interchangeable with another type of attachment device, such as a lanyard clip or a belt clip. Accordingly, different users of hand sanitizer dispenser may utilize their preferred type of clip.

Sanitizer encasement 120 may include a plastic shell that may be coupled to an underlying dispenser base via a hinge (not expressly shown in FIG. 1A) located near the top of dispenser 100. In some embodiments, sanitizer encasement 120 may be opened to allow a depleted pouch of hand sanitizer to be removed and a new pouch of hand sanitizer to be inserted. Sanitizer encasement 120 and underlying components that may be configured to receive a pouch of hand sanitizer are described in further detail below with reference to FIG. 2, FIG. 3A, and FIG. 3B.

Push plate 130 may include a shell that may be coupled to an underlying dispenser base (described below in reference to FIG. 4). In some embodiments, push plate 130 and/or its shell may be plastic or any other suitable material. In some embodiments, push plate 130 may be coupled to the underlying dispenser base via a spring-loaded coupling. Moreover, push plate 130 may be configured to actuate a sanitizer pump when pressed. In some embodiments, the position of push plate 130 may be biased by the semi-flexible nature of an underlying diaphragm pump in combination with or instead of being biased by the spring-loaded coupling described above. Such a semi-flexible diaphragm pump is described in further detail below with reference to FIG. 4. The outer surface of push plate 130 may be configured in a rounded manner and may be sized to fit in the palm of a user's hand. Accordingly, push plate 130 may allow a user to ergonomically squeeze the lower portion of dispenser 100 with the palm of one hand to actuate the internal sanitizer pump, which may in turn cause dispenser 100 to dispense a dose of sanitizer through dispenser opening 140. Push plate 130 and various components of dispenser 100 that may be located underneath push plate 130 are described in further detail below with reference to FIG. 4.

FIG. 1B illustrates a hand sanitizer dispenser 150, in accordance with certain embodiments of the present disclosure. In some embodiments, hand sanitizer dispenser 150 may include a lower pump encasement 160 and an inset push plate 170. In some embodiments, inset push plate 170 may operate in a similar manner to push plate 130 described above. For example, inset push plate 170 may be coupled to the underlying dispenser base via a spring-loaded coupling. Moreover, inset push plate 170 may be configured to actuate a sanitizer pump when pressed. In some embodiments, the position of inset push plate 170 may be biased by the semi-flexible nature of an underlying diaphragm pump in combination with or instead of being biased by the spring-loaded coupling described above. Inset push plate 170 may have a resting position that may be inset from a lower pump encasement 160, which may be configured to have a fixed position relative to the underlying dispenser base and diaphragm pump. The inset position of inset push plate 170 may prevent unintentional pressing of inset push plate 170. For example, if a user is wearing dispenser 150 and accidentally squeezes dispenser 150 when leaning against a countertop, the countertop may press on the lower pump encasement 160 rather than inset push plate 170. Accordingly, an unintentional pressing of inset push plate 170, and an unintentional dispensing of sanitizer, may be avoided.

Figure 2:
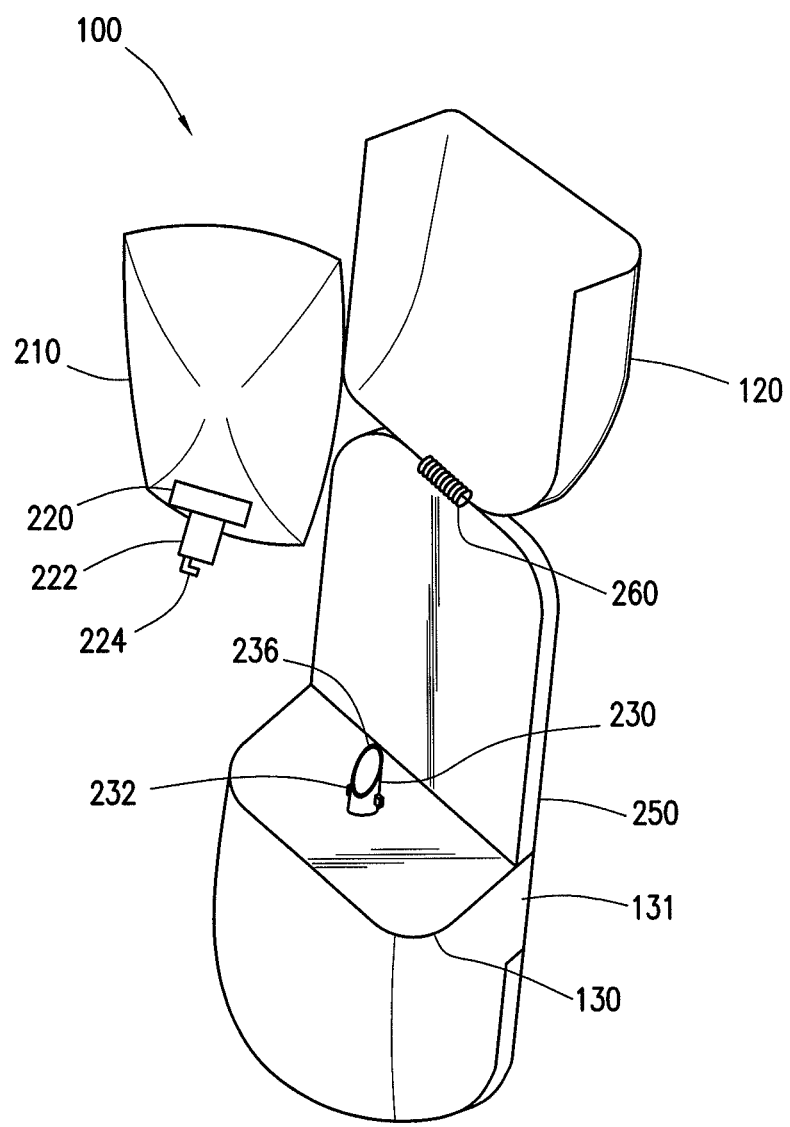
FIG. 2 illustrates a dispenser with a replaceable pouch of hand sanitizer, in accordance with certain embodiments of the present disclosure.

FIG. 2 illustrates dispenser 100 with a replaceable pouch 210 of hand sanitizer, in accordance with certain embodiments of the present disclosure.

In some embodiments, push plate 130 may be configured to prevent an unintentional pressing and unintentional dispensing of sanitizer. As shown in FIG. 2, push plate 130 may include a wrap-around portion 131. In some embodiments, wrap-around portion 131 may extend along the back side of dispenser 100 from one side of push plate 130 to the other side of push plate 130, such that push plate 130 and wrap-around portion 131 fully encircle at least a portion of the underlying components of dispenser 100. The wrap-around portion 131 may align with an indent in dispenser base 250. The configuration of push plate 130 and wrap-around portion 131 may prevent an unintentional dispensing of sanitizer. For example, if a user is wearing dispenser 100 and accidentally pushes dispenser 100 when leaning against a countertop, the force may be absorbed by a rigid coupling between the surface of push plate 130 and wrap-around portion 131 of push plate 130. Accordingly, an unintentional pressing on push plate 130 may be avoided. An intentional pressing of push plate 130, and in intentional dispensing of sanitizer, may then occur by the user cupping their hand about dispenser opening 140 at the bottom of dispenser 100, placing their fingers at a lower portion dispenser base 250 that is not encircled by wrap-around portion 131, placing their palm on the rounded surface of push plate 130, and squeezing push plate 130 and dispenser base 250 together.

As shown in FIG. 2, sanitizer encasement 120 may be coupled to dispenser base 250 via hinge 260. Accordingly, sanitizer encasement 120 may be opened to allow pouch 210, which may include a reservoir of sanitizer, to be inserted into dispenser 100. In some embodiments, pouch 210 may include a collapsible plastic bag and fitment 220. Fitment 220 may be made of plastic for example, and may have a portion sealed within the collapsible plastic bag of pouch 210 and a portion that extends to the outside of the collapsible bag. Fitment 220 may provide a path for sanitizer to flow from inside of the collapsible bag to outside the collapsible bag and into a feature of dispenser 100. Moreover, fitment 220 may provide features independent from the collapsible plastic bag of pouch 210 that may allow pouch 210 to be physically coupled to features of dispenser 100. For example, fitment 220 may include nozzle 222. Fitment 220 and nozzle 222 may be used to couple pouch 210 to dispenser 100 at pump intake 230. Dispenser 100 may pump and dispense the sanitizer in pouch 210, and the collapsible plastic bag of pouch 210 may collapse around the remaining portions of the sanitizer reservoir, and thus may maintain an air tight seal around the reservoir of sanitizer. After one pouch 210 has been depleted, it may be decoupled from dispenser 100 and replaced with another pouch 210. The coupling and decoupling of pouch 210 and dispenser 100 is described in greater detail below with reference to FIG. 3A and FIG. 3B.

Though pouch 210 may be describe above as including a collapsible plastic bag, in some embodiments the reservoir of hand sanitizer may be contained within any suitable type of enclosure. For example, pouch 210 may include a semi-flexible plastic bottle or any other suitable type of flexible, semi-flexible, or rigid enclosure.

FIG. 3A illustrates a coupling mechanism for hand sanitizer dispenser 100 and a replaceable pouch 210 of hand sanitizer, in accordance with certain embodiments of the present disclosure. As described above, pouch 210 may include fitment 220 and nozzle 222. Fitment 220 may be sealed within pouch 210 at or near pouch border 215, and nozzle 222 may extend from fitment 220 to the outside of the collapsible plastic bag. In some embodiments, fitment 220 and nozzle 222 may be configured to be coupled to pump intake 230 in order to provide a flow of sanitizer from pouch 210 to a pump. For example, in some embodiments, one or more twist-lock hooks 224 may extend from an end of nozzle 222. Such twist-lock hooks 224 may be configured to align with locking studs 232 which may be located on pump intake 230. Accordingly, nozzle 222 may be placed onto pump intake 230 and then twisted in a locking direction until twist-lock hooks 224 engage locking studs 232. After twist-lock hooks 224 engage locking studs 232, pouch 210, fitment 220, and nozzle 222 may be locked into position with pump intake 230.

Although fitment 220, nozzle 222, and twist-lock hooks 224 may be described above as separate components, the term "fitment," may, for the purposes of the present disclosure, refer to both fitment 220 and nozzle 222, and any fitment-locking device such as twist-lock hooks 224, which may be coupled to nozzle 222.

In some embodiments, nozzle 222 may include a seal 240. Seal 240 may keep sanitizer sealed within pouch 210 until pouch 210 is coupled to dispenser 100. In some embodiments, seal 240 may include a foil. Pump intake 230 may include a pointed end 236 that may pierce the foil of seal 240 as nozzle 222 is placed onto pump intake 230. After seal 240 is pierced, pump intake 230 may be in fluid contact with the reservoir of sanitizer that may be contained within pouch 210. In order to prevent leakage of air into the sanitizer pump, or leakage of sanitizer out of the dispenser 100, the outside surface of pump intake 230 may be configured to have a diameter that is approximately equal to or slightly less than the diameter of the inner surface of nozzle 222. Moreover, in some embodiments, pump intake 230 may include a sealing device, for example, o-ring 234. In some embodiments, o-ring 234 may form a circle around pump intake 230 and be made of a pliable material such as rubber, and thus may provide an air-tight seal to the coupling between nozzle 222 and pump intake 234.

The configuration of dispenser 100 and pouch 210 may allow pouch 210 to be disconnected and replaced after the sanitizer in pouch 210 has been depleted. For example, after pouch 210 has been depleted of its sanitizer, fitment 220 and nozzle 222 may be twisted in an unlocking direction to disengage twist-lock hooks 224 from locking studs 232 on pump intake 230. Accordingly, a used pouch 210 may be removed from dispenser 100 and replaced with a new pouch 210.

Figure 3B:
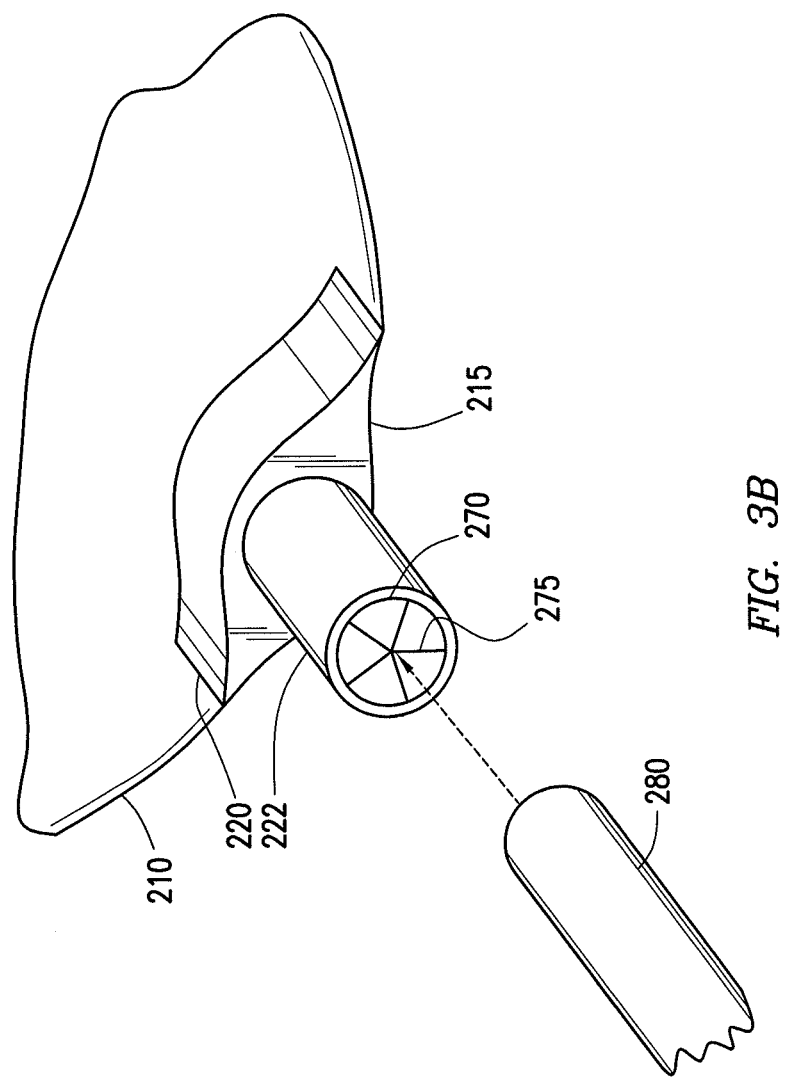
FIG. 3B illustrates a coupling mechanism for a hand sanitizer dispenser and a pouch, in accordance with certain embodiments of the present disclosure.

FIG. 3B illustrates a coupling mechanism for hand sanitizer dispenser 100 and a replaceable pouch 210 of hand sanitizer, in accordance with certain embodiments of the present disclosure. Pouch 210 may incorporate any other suitable attachment technique in place of or in combination with the twist-lock mechanism described above. For example, in some embodiments, nozzle 222 of pouch 210 may include a valve configured to engage with a dispenser intake. The valve may include any suitable type of valve such as a duck-billed valve, a check valve, or a flap valve. For example, in some embodiments, nozzle 222 may include flap valve 270 that may prevent sanitizer from flowing out of pouch 210 when pouch 210 is disconnected from dispenser 100. When pump intake 280 is inserted into nozzle 222, pump intake 280 may pierce the barrier formed by flap valve 270 and may physically hold one or more flaps 275 of flap valve 270 open, which may allow the sanitizer to be pulled out of pouch 210 by dispenser 100's pump. Moreover, the one or more flaps 275 of flap valve 270 may comprise a flexible material with a thickness suitable to provide a tight fit between inner surface of nozzle 222 and the outer surface of pump intake 280. Such a fit may lockably engage pouch 210 and dispenser intake 280 by holding pouch 210 in place until a user intentionally detaches pouch 210, and in particular nozzle 222, from pump intake 280. When such an embodiment of pouch 210 is removed from pump intake 280, flap valve 270 may re-close, and thus may prevent any remaining sanitizer from leaking out of pouch 210.

Though some embodiments of dispenser 100 are described above as including and/or operating with a replaceable pouch 210 of hand sanitizer, some embodiments of dispenser 100 may include and/or operate with a replaceable and/or refillable cartridge of hand sanitizer. For example, in some embodiments, dispenser 100 may omit sanitizer encasement 120, and instead may be configured to accept a replaceable cartridge that may have a plastic outer shell with a similar shape as sanitizer encasement 120. Such a cartridge may be configured to be coupled to (and subsequently decoupled from) dispenser 100 and/or pump intake 230 by any suitable coupling or attachment techniques. Moreover, such a cartridge may include an inner plastic pouch that may contain the sanitizer and prevent it from leaking. Upon attaching the cartridge to dispenser 100, a breaching mechanism contained either within the cartridge or within dispenser 100 may breach the plastic pouch in a controlled manner to allow sanitizer to flow from the cartridge to pump intake 230. Accordingly, the sanitizer in the cartridge may be pumped by dispenser 100 in the same or similar manner as described herein for the sanitizer in pouch 210.

Figure 4:
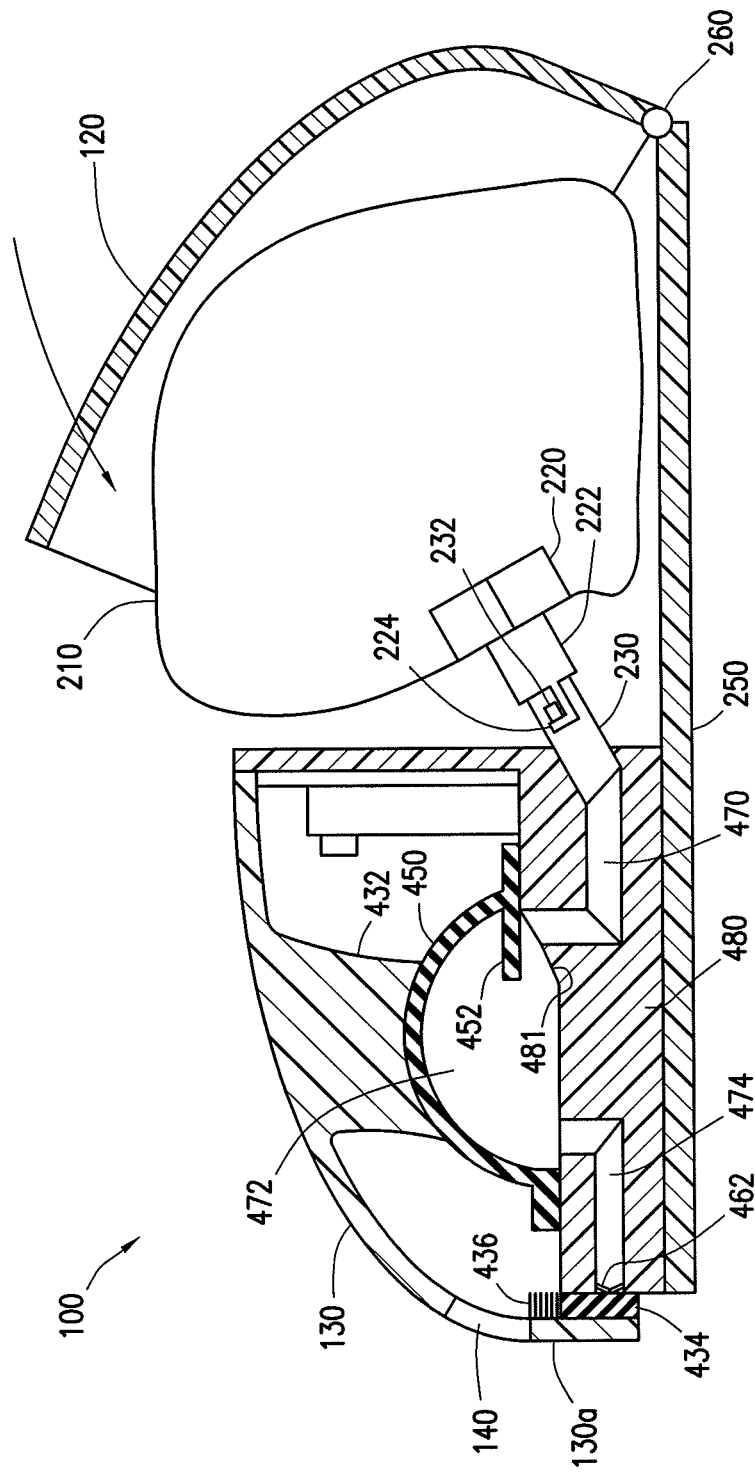
FIG. 4 illustrates a side cross-section view of a hand sanitizer dispenser, in accordance with certain embodiments of the present disclosure.

FIG. 4 illustrates a side cross-section view of a hand sanitizer dispenser, in accordance with certain embodiments of the present disclosure. Some embodiments of dispenser 100 may include pump housing 480, intake channel 470, intake valve 452, diaphragm 450, pump chamber 472, outlet channel 474, and outlet valve 462. Though FIG. 4 may illustrate some features of dispenser 100, and how those features may interact with one another, the features in FIG. 4 are not necessarily drawn to scale with respect to each other.

In some embodiments, diaphragm 450 may form a dome-like structure that may partially encircle pump chamber 472. Diaphragm 450 may include a flexible material that may collapse when pressed and recoil to its natural dome-like shape when released. In some embodiments, diaphragm 450 may be configured to bias the position of push plate 130. Accordingly, diaphragm 450 may be flexible enough to collapse when pressed by a user via push plate 130 and/or pump actuator 432. Moreover, diaphragm may be flexible enough such that it may avoid being brittle. Diaphragm 450 may also have a sufficient hardness and/or stiffness such that it may resist mechanical fatigue despite repeated use. Further, diaphragm 450 may have a sufficient hardness and/or stiffness such that it may recoil with enough force to create a sufficient vacuum to pull a gel-type sanitizer into pump chamber 472 upon being released. In some embodiments, diaphragm 450 may comprise a rubberized material with a hardness of approximately 30 durometers to approximately 90 durometers. In some embodiments, diaphragm 450 may comprise a rubberized material with a hardness of approximately 60 durometers. Moreover, diaphragm 450 may be formed by a material that may resist reacting with the ingredients of the sanitizer, and thus may resist fatiguing as a result of long-term exposure to sanitizer. For example, in some embodiments, diaphragm 450 may be formed by a silicone rubber that may be resistant to long-term exposure to the active ingredients in various types of sanitizers, including alcohol-based sanitizers and other types of sanitizers that may include, for example, isopropanol, ethanol, n-propanol, and/or povidone-iodine.

Intake channel 470 may form a channel through one side of pump housing 480. In some embodiments, intake channel 470 may be coupled at one end to pump intake 230. Accordingly, intake channel 470 may be in fluid communication with a reservoir of sanitizer that may be inside pouch 210, which as described above with reference to FIGS. 2 and 3, may be coupled to dispenser 100 at pump intake 230. For the purposes of the present disclosure, one feature may be in "fluid communication" with another feature if fluid and/or gel may be able to flow, or be allowed to flow, from the one feature to the other feature. Intake channel 470 may also be in fluid communication with pump chamber 472, depending on the state of intake valve 452. In some embodiments, intake valve 452 may be a one-way valve. Moreover, in some embodiments, intake valve 452 may be a one-way flap valve. When intake valve 452 is open, intake valve 452 may allow sanitizer to flow from intake channel 470 into pump chamber 472. However, intake valve 452 may close to prevent a flow of sanitizer from pump chamber 472 into intake channel 470. In some embodiments, pump housing 480 may include a sloped lip 481. In embodiments where intake valve 452 is a one-way flap valve, the flap forming intake valve 452 may align with the slope of lip 481 when intake valve 452 is in a closed state.

In some embodiments, the flap forming intake valve 452 may be formed by the same piece of material forming diaphragm 450. Accordingly, in some embodiments, intake valve 452 may be configured in an economic manner that reduces material costs and production costs.

Although an embodiment of intake valve 452 may be described above as a one-way flap valve, intake valve 452 may include any suitable one-way valve, for example, a duck-billed valve or a check valve. Moreover, intake valve 452 may be located at any position between pump chamber 472 and the reservoir of hand sanitizer within pouch 210, in order to prevent back-flow from pump chamber 472 to the reservoir of hand sanitizer when the pump is actuated. For example, in various embodiments, intake valve 452 may be located within intake channel 470, pump intake 230, nozzle 222, or fitment 220. For the purposes of the present disclosure, the term "dispenser intake" may refer to any channel, feature, or area, that may be located adjacent to the input of intake valve 452.

Outlet channel 474 may form a channel through a second side of pump housing 270. In some embodiments, outlet channel 474 may be in fluid communication with pump chamber 472. Moreover, outlet channel 474 may be in fluid communication with dispenser opening 140 depending on the state of outlet valve 462. In some embodiments, outlet valve 462 may be a one-way valve. Moreover, in some embodiments, outlet valve 462 may be a one-way flap valve. In such embodiments, outlet valve 462 may contain two flaps that may separate in an open state to allow sanitizer to flow out of outlet channel 474, and may also come together in a closed state to prevent the back-flow of air and/or sanitizer from outside dispenser 100 into outlet channel 474. For the purposes of the present disclosure, the end of the channel that includes outlet channel 474 may be referred to as the dispenser outlet. Moreover, in embodiments where outlet valve 462 may be located near the end of outlet channel 474, the output of outlet valve 462 may also be referred to as the dispenser outlet.

Though an embodiment of outlet valve 462 may be described above as a one-way flap valve with two flaps, outlet valve 462 may include any suitable one-way valve, for example, a single-flap flap valve, a duck-billed valve, or a check valve. Moreover, outlet valve 462 may be located at any position between pump chamber 472 and the end of outlet channel 474 in order to prevent the back-flow of air and/or sanitizer from outside dispenser 100 into pump chamber 472 when diaphragm 450 recoils.

As described above with reference to FIG. 1A, the sanitizer pump may be actuated by a user applying a force to push plate 130. Push plate 130 may include pump actuator 432. Pump actuator 432 may be configured such that when a user presses down on push plate 130, pump actuator 432 presses down on diaphragm 450. At this time, the fluid pressure inside of pump chamber 472 may increase. In embodiments where intake valve 452 is a one-way flap valve, this pressure may force the flap of intake valve 452 to close. Thus, sanitizer may be prevented from back-flowing into intake channel 470, pump intake 230, and/or pouch 210.

When a user presses push plate 130, pump actuator 432 may press diaphragm 450, and the fluid pressure inside of pump chamber 472 may force sanitizer out of pump chamber 472 through outlet channel 474. At this time, the flaps of outlet valve 462 may open and allow sanitizer to flow out of outlet channel 474. Moreover, when push plate 130 is pressed downward, dispenser opening 140 may align with the dispenser outlet, which may include the end of outlet channel 474 and/or the output of outlet valve 472. Accordingly, a dose of sanitizer may be dispensed to a user.

After a user presses and subsequently releases push plate 130, push plate 130 and pump actuator 432 may return to a resting position. An example of such a resting position is illustrated in FIG. 4. In some embodiments, the position of push plate 130 may be biased by the semi-flexible nature of diaphragm 450, which may force diaphragm 450 to return to its resting dome-like shape when the force on diaphragm 450 is released. The return of diaphragm 450 to a resting position may force push plate 130 to return to push plate 130's resting position.

When diaphragm 450 recoils to its resting dome-like shape, it may create a vacuum force within pump chamber 472. At this time, the outlet valve 462 may close and may prevent air and/or sanitizer from back-flowing into outlet channel 474 and pump chamber 472.

As diaphragm 450 recoils, the vacuum pressure within pump chamber 472 may cause intake valve 452 to open. Accordingly, the vacuum pressure within pump chamber 472 may pull sanitizer from the reservoir of sanitizer within pouch 210 into pump chamber 472. After diaphragm 450 has fully recoiled, pump chamber 472 may be re-filled with sanitizer from pouch 210 and may be ready for the next dispensing action.

Dispenser 100 may also include features that prevent any excess sanitizer from leaking out after a dose of sanitizer has been dispensed to a user. For example, a stopper 434 may be coupled to an inside wall of a lower portion of push plate 130a. Stopper 434 may be aligned with the dispenser outlet (e.g., the tip of outlet channel 474 and/or the output of outlet valve 462) when push plate 130 is in a resting position. In some embodiments stopper 434 may be formed by a rubberized material. Accordingly, stopper 434 may form a seal over the dispenser outlet between dispensing actions, and thus may prevent sanitizer from leaking between dispensing actions.

Further, dispenser 100 may include features that may prevent any excess sanitizer that may be left at the tip of outlet channel 474 and/or the output of outlet valve 462 from forming a residue that may clog the dispenser outlet. For example, brush 436 may be coupled to an inside wall of a lower portion of push plate 130a. As push plate 130 returns to its resting position after a dispensing action, brush 436 may pass over the dispenser outlet, e.g., the end of outlet channel 474 and/or the output of outlet valve 462. In some embodiments, bristles 436 may include an absorbent material. Accordingly, bristles may wipe away and/or absorb any sanitizer residue that may be left over on the tip of outlet channel 474 and/or on the output of outlet valve 462 after a dispensing action.

Figure 5:
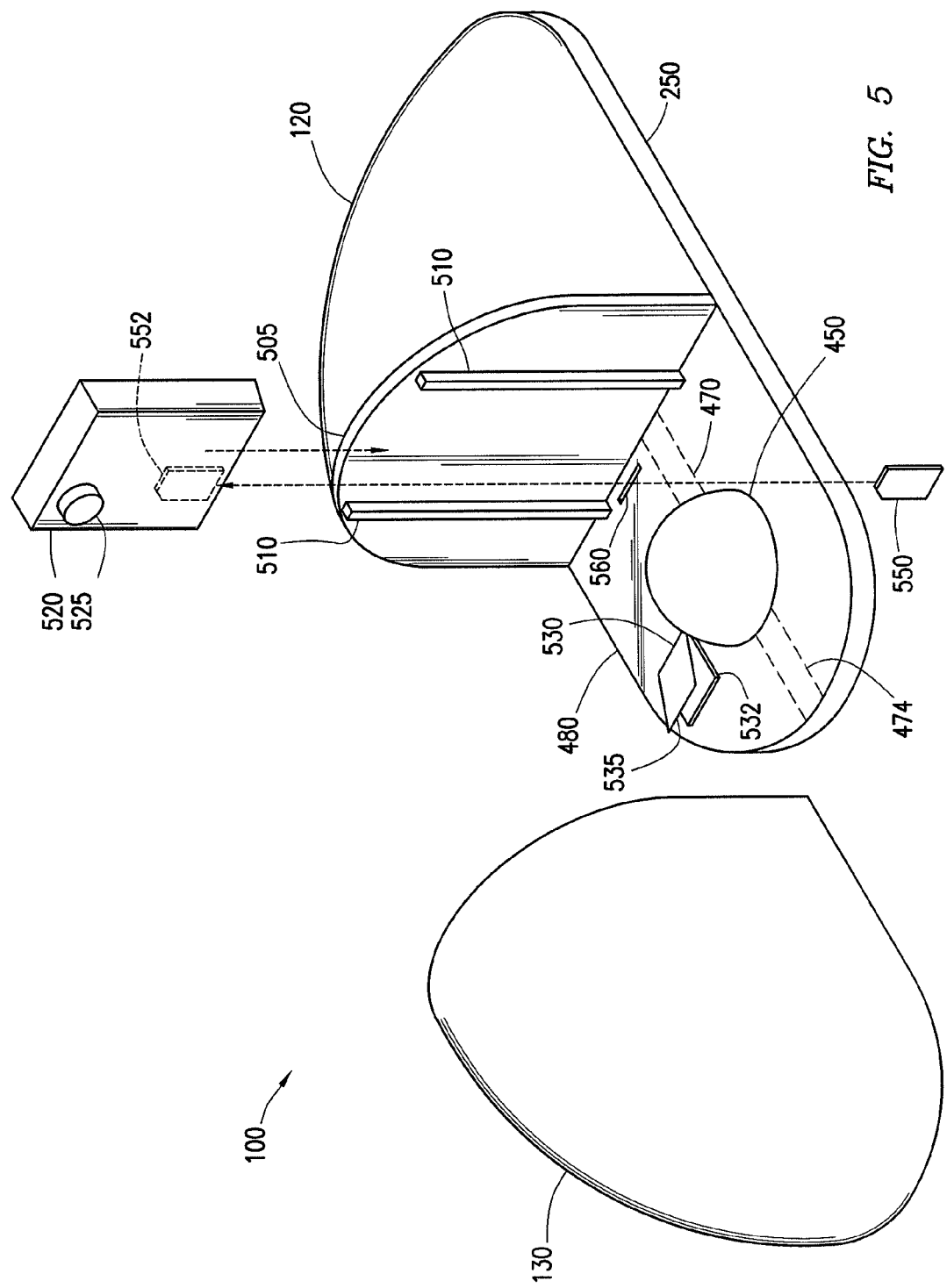
FIG. 5 illustrates an exploded view of certain components within a hand sanitizer dispenser, in accordance with certain embodiments of the present disclosure.

FIG. 5 illustrates an exploded view of certain components within hand sanitizer dispenser 100, in accordance with certain embodiments of the present disclosure. As shown in FIG. 5, dispenser 100 may include contact device 530 and electronic module 520.

In some embodiments, contact device 530 may be located to one side of diaphragm 450. Contact device 530 may include base 532 and lever 535. Base 532 may be coupled to pump housing 480. Lever 535 may extend from base 532 at an angle. Lever 535 may be spring loaded and may normally rest in an upward sloped position. Dispenser 100 may include a lever actuator (not expressly shown), which, similar to pump actuator 432, may extend downward from the inside wall of push plate 130. As push plate 130 is pressed downward by a user during a dispensing action, the lever actuator may press downward on lever 535.

In some embodiments, lever 535 may have a predefined range of motion from its resting position to the point at which it may be stopped by the base 532. In turn, push plate 130 may also have a predefined range of motion from its resting position to a fully pressed position. Because push plate 130 may have a predefined range of motion, the extent to which diaphragm 450 may be pressed may remain consistent for repeated dispensing actions. As opposed to a system in which a user directly pushes a pumping mechanism such as diaphragm 450, and may do so in an inconsistent manner across multiple dispensing actions, the interaction between push plate 130 and diaphragm 450 in dispenser 100 may ensure that diaphragm 450 is pressed in a consistent manner. Accordingly, dispenser 100 may dispense a consistent dose of sanitizer across multiple dispensing actions. Moreover, in some embodiments, contact device 530 may be configured to mechanically sense when lever 535 is fully depressed and may make a clicking noise when lever 535 is fully depressed. Accordingly, contact device 530 may operate as a mechanical sensor configured to emit an audible indicator when lever 535, and in turn push plate 130, reach the end of their predefined respective ranges of motion. Because push plate 130's predefined range of motion may ensure a consistent dose of sanitizer, the audible feedback may inform the user that the pump has been fully actuated and that a full and consistent dose of sanitizer has been dispensed. Although, push plate 130 may be described above as having a predefined range of motion corresponding to the range of motion of lever 535, push plate 130 may have a range of motion that is predefined by any other suitable technique.

Another factor that may affect the consistency of the administered dose may be back-flow of air and/or sanitizer through outlet channel 474 when diaphragm 450 recoils. However, as described above with reference to FIG. 4, outlet valve 462 may prevent the back-flow of sanitizer through outlet channel 474 when diaphragm 450 recoils. Accordingly, outlet valve 462 may further improve the consistency of the dose of sanitizer that is administered with every dispensing action.

The dose amount for each dispensing action may depend on the fraction of the active ingredient in a given sanitizer (e.g., the alcohol content of a given sanitizer), and the amount of the active ingredient that is required for an effective hand cleansing. An effective dose for typical gel sanitizers may range, for example, from 0.75 mL to 1.50 mL. For embodiments of dispenser 100 designed to operate with such typical gel sanitizers, the size of diaphragm 450 and the range of motion for depressing diaphragm 450 may accordingly be configured to pump a dose of approximately 0.75 mL to 1.50 mL during each dispensing action. In other embodiments, the size of diaphragm 450 and the range of motion for depressing diaphragm 450 may be configured to pump a lesser or a greater amount of a given sanitizer depending the required dose of sanitizer.

Electronic module 520 may be configured to record and transmit information regarding dispensing actions. In some embodiments, electronic module 520 may include contact switch 525 that may be used to sense a dispensing action. Dispenser 100 may include a switch actuator (not expressly shown) that may be coupled to and/or extend from the inner surface of push plate 130, similar to pump actuator 432 described above. When push plate 130 is pressed during a dispensing action, the switch actuator may engage contact switch 525 and contact switch 525 may sense the dispensing action. Components within electronic module 520 that are used to record the occurrence of a dispensing action and to transmit such data to a network are described below with reference to FIG. 6.

In some embodiments, electronic module 520 may include a unique user identifier to distinguish between different users that may use one or more units of dispenser 100. In some embodiments, a user identifier may be stored in a non-volatile memory permanently located within electronic module 520. For such embodiments, each hospital employee may be assigned an electronic module 520 and may be identified by the user identifier contained within their assigned electronic module 520. Electronic module 520 may be configured to be interchangeably inserted into and out of different dispenser 100 units. Accordingly, the user identifier may be user-specific rather than dispenser-specific.

In some embodiments, push plate 130 may be configured to be easily detached from and re-attached to dispenser 100 so that a user may easily remove their electronic module 520 from one dispenser 100 and/or insert their electronic module 520 into another dispenser 100. To aid such functionality, dispenser 100 may include rails 510, which may be configured to allow electronic module 520 to be easily slid into place and secured along dispenser wall 505. Though in some embodiments electronic module 520 may be secured along dispenser wall 505, in other embodiments electronic module may be secured to or within dispenser 100 by any suitable means in any suitable location. For example, in some embodiments, an electronic module may be inserted into an opening in the bottom of dispenser base 250. In some embodiments, an electronic module may be inserted into the bottom of dispenser base 250 similar to the way AA-batteries are inserted into the bottom of a common television remotes. For such electronic modules, a contact switch or any other type sensor may be configured to sense a dispensing action.

In some embodiments, electronic module 520 may be configured to be placed within dispenser 100 on a long-term basis. For such embodiments, each hospital employee may be assigned a transferable memory card 550 that may include a user identifier stored in non-volatile memory. The user identifier may be user-specific rather than dispenser-specific.

Memory card 550 may be any suitable memory device. For example, some embodiments of memory card 550 may include a secure-digital card ("SD-card"), a micro SD-card, or a Universal Serial Bus ("USB")-drive. To accommodate the use of memory card 550, electronic module 520 may include a memory receptacle 552, in which memory card 550 might be placed in order to be brought into electrical coupling with other electrical components within electronic module 520. Such other electrical components within electronic module 520 are described in further detail below with respect to FIG. 6. Moreover, to accommodate the placement of memory card 550 into memory receptacle 552, dispenser 100 may include opening 560, which may extend through the bottom of dispenser base 250. Opening 560 may align with memory receptacle 552 when electronic module 520 is placed in dispenser 100 along dispenser wall 505. Accordingly, memory card 550 may be inserted through the bottom of dispenser 100's opening 560, and into electronic module 520's memory receptacle 552.

Such embodiments may provide flexibility to the way that hospital employees, for example, may use individual units of dispenser 100. For example, different hospital employees, including those working at different times, may share a common pool of generic dispenser 100 units, and may individually participate in a hand hygiene monitoring program by simply inserting their respective electronic modules 520 and/or memory cards 550 into dispenser 100 without the need for a dispenser-specific identifier. Moreover, if a dispenser 100 malfunctions, a hospital employee may simply insert their assigned electronic module 520 or memory card 550 into another dispenser 100 to continue participating in the hand hygiene monitoring program.

Figure 6:
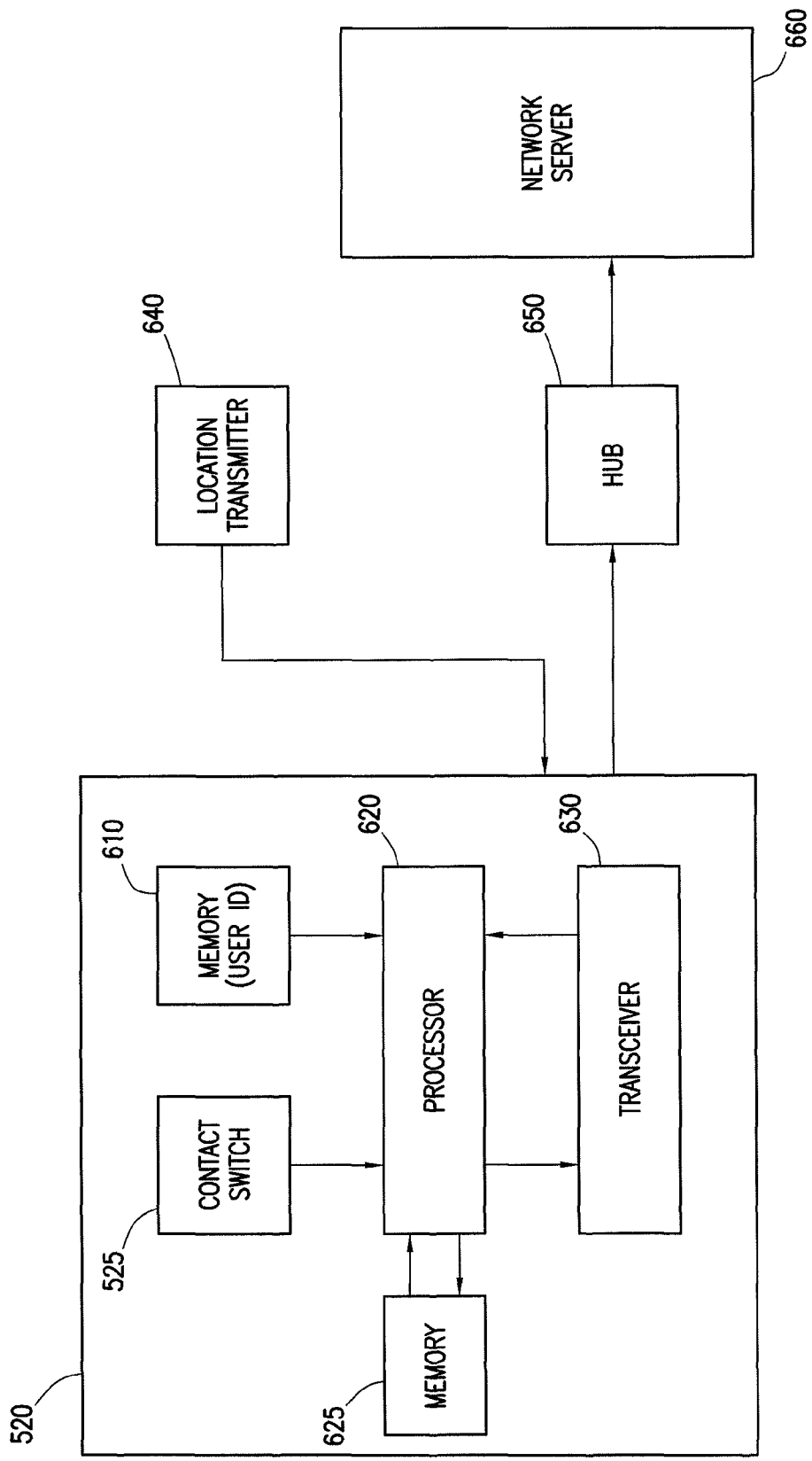
FIG. 6 illustrates a block diagram of an electronic module and network devices with which the electronic module may communicate, in accordance with certain embodiments of the present disclosure.

FIG. 6 illustrates a block diagram of electronic module 520 and network devices with which electronic module 520 may communicate, in accordance with certain embodiments of the present disclosure. Electronic module 520 may include contact switch 525, user identifier memory 610, processor 620, memory 625, and transceiver 630. Moreover, electronic module 520 may be configured to communicate with location transmitter 640 and hub 650, which may in turn be configured to communicate with network server 660.

In a hospital environment, for example, personal hand-sanitizer dispensers may be carried and used by users such as doctors and nurses. As described in greater detail below, each dispenser may include an electronic module 520 which may be configured to communicate with different hubs 650 that may be installed in different locations throughout the hospital. Each hub 650 may be configured to add location information to any information received from an electronic module 520, and may transmit that location information along with any user identifier and/or dispense indicator received from an electronic module 520 to network server 660. For example, electronic module 520 may be configured to periodically transmit a user identifier to a location-specific hub 650, which may allow network server 660 to track the location of electronic module 520 over time. Moreover, electronic module 520 may be configured to transmit a dispense indicator along with the periodic transmission of the user identifier to the location-specific hub 650 when a dispensing action has occurred in the previous time period. Accordingly, network server 660 may track the location of a user over time as well as the time and location of any dispensing actions (i.e., instances of a user sanitizing their hands) for that user.

Processor 620 may comprise, for example, a microprocessor, microcontroller, digital signal processor (DSP), application specific integrated circuit (ASIC), or any other digital or analog circuitry configured to interpret and/or execute program instructions and/or process data. In some embodiments, processor 620 may interpret and/or execute program instructions and/or process data stored in memory 625. Memory 625 may be configured in part or whole as application memory, system memory, or both. Memory 625 may include any system, device, or apparatus configured to hold and/or house one or more memory modules. Each memory module may include any system, device or apparatus configured to retain program instructions and/or data for a period of time (e.g., computer-readable storage media). Instructions, logic, or data for configuring the operation of electronic module 520, for example, configurations of components such as transceiver 630, may reside in memory 625 for execution by processor 620.

Electronic module 520 may include a user identifier memory 610, which may store a user identifier. As described above with reference to FIG. 5, in some embodiments user identifier memory 610 may include a non-volatile memory permanently located within electronic module 520. In some embodiments, user identifier memory 610 may include an interchangeable non-volatile memory such as memory card 550. Processor 620 may be configured to read user identifier memory 610 and may instruct transceiver 630 to transmit the user identifier to the nearest location-specific hub 650 at specified times (e.g., at a regular interval of 15 seconds).

In some embodiments, electronic module 520 may be configured to periodically transmit the user identifier to the nearest location-specific hub 650. Time information may be added to the periodically transmitted user identifier in any suitable manner. In some embodiments, electronic module 520 may include a clock that tracks the time of day. In such embodiments, electronic module 520 may transmit time information to hub 650 along with the user identifier for each periodic transmission of the user identifier.

In some embodiments, the task of adding time information to each periodic transmission of the user identifier may be allocated to hub 650 or network server 660 in order to reduce the amount of circuitry needed in electronic module 520 and to reduce the amount of data that is transmitted from electronic module 520. For example, hub 650 may include a clock and may record the time at which the user identifier was received from electronic module 520. Hub 650 may then transmit the user identifier, hub 650's location information, and the time information to network server 660. This time information may be used by network server 660 along with the location identifier to track the to track the location of a user over a period of time, and accordingly may be referred to herein as "user-time information." In some embodiments, the task of adding user-time information to each periodic transmission of the user identifier may be allocated to network server 660. For example, network server 660 may include a clock and may record the time at which the user identifier and the location information were received by network server 660 from hub 650. Because hub 650 may transmit the user identifier and hub 650's location information to network server 660 shortly after receiving the user identifier from electronic module 520, the user-time information determined at network server 660 may accurately represent the time at which electronic module 520 transmitted the user identifier to hub 650. Accordingly, in any of the above described embodiments, tracking system 200 may track the location of electronic module 520 over time as a user carries dispenser 205 and/or electronic module 520 to different locations equipped with different units of location-specific hub 650.

As described above with reference to FIG. 5, electronic module 520 may include a sensor, such as contact switch 525, which may be engaged during dispensing actions. Contact switch 525 may sense when a user pushes down on a dispenser's push plate to engage the dispensers pump and the dispense a dose of hand sanitizer. Although some embodiments may utilize a contact switch to sense a dispensing action, any suitable sensor may be configured to sense any force, motion, or other activity that may occur during a dispensing action, for example, the activation of a sanitizer pump and/or the flow of sanitizer out of a dispenser outlet.

In response to sensing a dispensing action, contact switch 525 may communicate the dispensing, and processor 620 may record a dispense indicator. Processor 620 may record the dispense indicator in memory 625. In some embodiments, transceiver 630 may transmit the dispense indicator along with the next periodic transmission of the user identifier to a location-specific hub 650.

Dispense-time information may be determined by any suitable means. As described above, the electronic module 520 may include a clock that tracks the time of day. In such embodiments, electronic module 520 may add dispense-time information to the dispense indicator. Accordingly, during the next periodic transmission of the user identifier after a dispensing action, electronic module 520 may transmit the user identifier, user-time information, the dispense indicator, and dispense-time information to hub 650. Hub 650 may then relay that information along with hub 650's location information to network server 660.

As described above, in some embodiments, the task of adding the user-time information may be allocated to hub 650 or network server 660 in order to simplify electronic module 520's circuitry and to minimize the amount of data that is transmitted from electronic module 520. In such embodiments, rather than having a clock that tracks the time of day, electronic module 520 may include a timer that may count the time between successful periodic transmissions of the user identifier. For example, in some embodiments, transceiver 630 may be programmed to periodically transmit the user identifier every fifteen seconds. If hub 650 successfully receives the transmission of the user identifier, hub 650 may confirm the receipt of the transmission by sending what is known in the art as an "acknowledgement packet" to the electronic module 520. In some embodiments, the acknowledgement packet may be a binary signal indicating receipt. In some embodiments, the acknowledgement packet may identify which hub 650 received the transmission. After electronic module 520 receives an acknowledgement packet, electronic module 520's timer may reset and may begin counting from zero. If a dispensing action occurs ten seconds after the acknowledgement packet was received, processor 620 may record a time stamp of ten seconds to memory 625 along with the dispense indicator. In some embodiments, the dispense indicator may include the time stamp. Moreover, in some embodiments, the time stamp itself may be the dispense indicator. A second periodic transmission of the user identifier may occur, for example, fifteen seconds after a first periodic transmission of the user identifier. During this second periodic transmission of the user identifier, transceiver 630 may transmit the dispense indicator and/or time stamp along with the user identifier to hub 650. If electronic module 520 receives an acknowledgment that this second periodic transmission was received by hub 650, electronic module 520 may delete the dispense indicator and/or time stamp and restart its timer.

In some situations, electronic module 520 may not receive an acknowledgement packet from hub 650 after a periodic transmission of the user identifier. For example, a user may carry their electronic module 520 outside of the range of any hub 650 located in a hospital. In such situations, the timer of electronic module 520 may continue running, and any recorded dispense indicators and/or time stamps, may continue to be stored by electronic module 520 until the next successful periodic transmission of the user identifier (e.g., the next periodic transmission for which an acknowledgement packet is received). For example, if a first periodic transmission of the user identifier is acknowledged, the timer may be reset and any dispense indicators and/or time stamps may be discarded. If a dispensing action is sensed ten seconds after the first periodic transmission occurs, a time stamp of ten seconds may be recorded. A second periodic transmission of the user identifier may occur fifteen seconds after the first periodic transmission. Accordingly, a time period of fifteen seconds and the time stamp of ten seconds may be transmitted with the second periodic transmission of the user identifier. If no acknowledgment is received (e.g., because electronic module 520 is outside the range of any hub 650), the timer may continue running and electronic module 520 may continue to store the time stamp of ten seconds. A third periodic transmission of the user identifier may then occur thirty seconds after the first periodic transmission. Accordingly, a time period of thirty seconds and the time stamp of ten seconds may be transmitted with the third periodic transmission of the user identifier. If an acknowledgment is received (e.g., because electronic module 520 has come back into range of hub 650), electronic module 520 may restart its timer and discard the successfully transmitted time stamp.

In some embodiments, the task of calculating a dispense time based on the time period and the dispense indicator and/or time stamp from electronic module 520, may be allocated to hub 650 or network server 660. For example, hub 650 may include a clock that tracks the time of day. Hub 650 may calculate dispense-time information based on the clock and the time period and the dispense indicator and/or time stamp received from electronic module 520. Hub 650 may calculate the dispense-time information by subtracting the time period from the time at which hub 650 received the dispense indicator and/or time stamp from electronic module 520, and then adding the time of the time stamp. For example, hub 650 may receive a time period of fifteen seconds and dispense indicator with a time stamp of ten seconds at 11:40:30 AM. Hub 650 may then calculate a dispense-time of 11:40:25 AM. Hub 650 may then transmit the user identifier, hub 650's location information, the dispense indicator and/or time stamp, and the dispense-time information to network server 660. In some embodiments, the calculated dispense-time information may itself indicate that a dispensing action occurred, and accordingly the dispense indicator and/or time stamp may be omitted from the transmission from hub 650 to network server 660.

In some embodiments, the dispense-time information may be calculated at network server 660. In such embodiments, hub 650 may relay the time period and dispense indicator and/or time stamp received from electronic module 520 to network server 660 along with the user identifier and location information shortly after receiving the dispense indicator and/or time stamp from electronic module 520. Network server 660 may then calculate the dispense-time information based on network server 660's clock, the time period, and the dispense indicator and/or time stamp received from electronic module 520 via hub 650. Network server 660 may calculate the dispense-time information by subtracting the time period from the time at which network server 660 received the dispense indicator and/or time stamp from hub 650, and then adding the time of the time stamp. For example, network server 660 may receive a time period of fifteen seconds and dispense indicator with a time stamp of ten seconds at 11:40:30 AM. Network server 660 may then calculate a dispense-time of 11:40:25 AM.

As described above, in some embodiments, location information may be added to any transmission from electronic module 520 at hub 650. In some embodiments, however, electronic module 520 may be configured to receive location information and to transmit that location information with the above described dispense indicator and/or user identifier. For example, each room in a hospital may be equipped with a designated location transmitter 640 that may include a unique location identifier associated with that room. When a user enters a hospital room with their dispenser, transceiver 630 may receive a signal from that room's location transmitter 640 including the location identifier. Electronic module 520 may then transmit the location identifier along with any user identifier and/or dispense indicator to a hospital's network server 660 via hub 650. In some embodiments, for example embodiments in which hub 650 is a mobile device, location transmitter 640 may be a stationary device independent from hub 650. In some embodiments, for example embodiments in which hub 650 is a location-specific device installed in a stationary location, location transmitter 640 may be located within hub 650.

In some embodiments, transceiver 630 of electronic module 520 may be configured to transmit and/or receive information on any suitable wired or wireless communications platform. For example, transceiver 630 may be configured to communicate with location transmitter 640 and/or hub 650 via Bluetooth, Wi-Fi, a micro-power wireless communication protocol such as the Adaptive Network Topology ("ANT") protocol, or any other suitable wireless communication protocol. Moreover, in some embodiments, electronic module 520 may include an RFID tag. In some embodiments, hub 650 in a hospital room may include an RFID reader and may read the RFID tag included in dispenser 100 to identify the presence of the user to which dispenser 100 may be assigned.

In some embodiments, electronic module 520 may be powered by one or more batteries that may be contained within electronic module 520. For example, electronic module 520 may contain one or more button cell batteries, coin cell batteries, lithium cell batteries, or any other suitable type of batteries.

To conserve battery power, electronic module 520 may, in some embodiments, be configured with a minimal amount of circuitry to perform the above-described functions. For example, as described above, electronic module 520 may be configured with a timer that may count the time between the periodic transmissions of the user identifier, but may otherwise omit a clock that tracks the time of day, in order to reduce the amount of circuitry included in electronic module 520 and to reduce the amount of data transmitted from electronic module 520. Moreover, in some embodiments, memory 625 may include a limited amount of memory to which processor 620 may record a dispense indicator and/or time stamp. In some embodiments, after one dispense indicator is recorded and transmitted, processor 620 may effectively discard that dispense indicator by either disregarding it or overwriting that dispense indicator with a subsequent dispense indicator. For some embodiments, such a minimalist design may allow electronic module 520 to conserve energy and thus operate with the same battery for a long period of time. In some embodiments, electronic module 520 may transmit any suitable number of dispense indicators and/or time stamps. For example, in some embodiments, memory 625 may include enough memory to include fourteen dispense indicators (including fourteen time stamps). In such embodiments, electronic module 520 may also be configured to receive and store into memory 625 location information from location transmitter 640. Over a period of time, processor 620 may record fourteen dispense indicators to memory 625 corresponding to fourteen different dispensing actions that may occur between successful transmissions to a location-specific hub 650. In some cases, multiple dispensing actions may occur in between normal periodic transmissions of the user identifier. In other cases, multiple dispense indicators and/or time stamps may be recorded while electronic module 520 is out of the wireless communication range of any hub 650. In response to the next successful periodic transmission of the user identifier when electronic module 520 is in range of a location-specific hub 650, for example, transceiver 630 may transmit all fourteen dispense indicators and/or time stamps to hub 650, and processor 620 may then discard the multiple dispense indicators and/or time stamps stored in memory 625.

In some embodiments, a micro-power wireless communication protocol such as the ANT protocol may be utilized by components within electronic module 520, e.g., processor 620 and/or transceiver 630, in order to optimize battery life. Micro-power transceivers (e.g., ANT transceivers) may conserve power by operating in a low-power "sleep" mode between data transmissions. In some embodiments, transceiver 630 may be programmed to "wake up" to transmit data at a programmed time interval and/or at every dispensing action, and otherwise operate in a sleep mode between transmissions. For example, in some embodiments, transceiver 630 may be programmed to wake up every fifteen seconds to transmit a user identifier and any recorded dispense indicators to the nearest room-specific hub 650 in a hospital network. Accordingly, the network server 660 may track the location of a user as that user travels, for example, to different hospital rooms throughout a work shift. Network server 660 may also track the times and the locations at which a user sanitized their hands throughout a work shift. Thus, network server 660 may monitor whether a user has complied with hand hygiene protocols, such as a rule requiring hospital employees to sanitize their hands every time they enter a patient room.

The time interval at which transceiver 630 may be programmed to wake up in order to transmit a user identifier may depend on a trade-off between power consumption and the desired resolution for tracking a user's location. Shorter time intervals may provide greater resolution with respect to where a hospital employee carrying dispenser 100 traveled and when, but may consume more power over a period of time due to the more frequent transmissions. On the other hand, longer time intervals may conserve power but may not provide the necessary resolution. In some applications with relaxed power consumption requirements and relaxed resolution requirements, transceiver 630's wake-up time interval may be programmed to be anywhere from less than approximately one second to greater than approximately one minute. For other applications that require conserving energy as well as providing a enough resolution to track the room-to-room movement of a user, transceiver 630's wake-up interval may correspond with the amount of time that it may take a hospital employee to walk at an average pace from one location of interest (e.g., a first patient room) to another location of interest (e.g., a second patient room). For such applications, transceiver 630's wake-up time interval may be programmed to be from approximately five seconds to approximately twenty-five seconds. In some embodiment, transceiver 630's wake-up time interval may be approximately fifteen seconds.

Although electronic module 520 may be described herein as being configured to operate in conjunction with a dispenser, in some embodiments, electronic module 520 may be operated independently from a dispenser. For example, for some embodiments, a user may carry electronic module 520 separately from a dispenser. For such embodiments, the dispenser may be any suitable mobile or stationary dispenser. For example, the dispenser may be implemented by a dispenser installed on the wall of hospital room. Moreover, in some embodiments, electronic module 520 may include any suitable sensor configured to sense a dispensing action by any suitable technique. For example, in some embodiments, a dispenser may be mounted on a wall in a hospital room and may be configured transmit a wireless signal each time it dispenses a dose of hand sanitizer. For such embodiments, electronic module 520 may include a sensor configured to sense the wireless signal from the stationary dispenser and may communicate the sensing of the dispensing action to processor 620. Electronic module 520 may record a dispense indicator and/or time stamp and transmit that information to hub 650 in the same manner as describe above. In some embodiments, electronic module 520 may include a sensor that may be configured to be independently activated by a user after the user washes or sanitizes their hands. For example, in embodiments that include a contact switch (e.g., contact switch 525 described in reference to FIG. 5), the user may wash and/or sanitize their hands and then push the contact switch. For the purposes of the present disclosure, any action by which a sensor of electronic module 520 may be triggered (e.g., by automatically sensing a dispensing action or by receiving a press from a user who has washed or sanitized their hands) may be referred to as electronic module 520 sensing a dispensing action.

Figure 7:
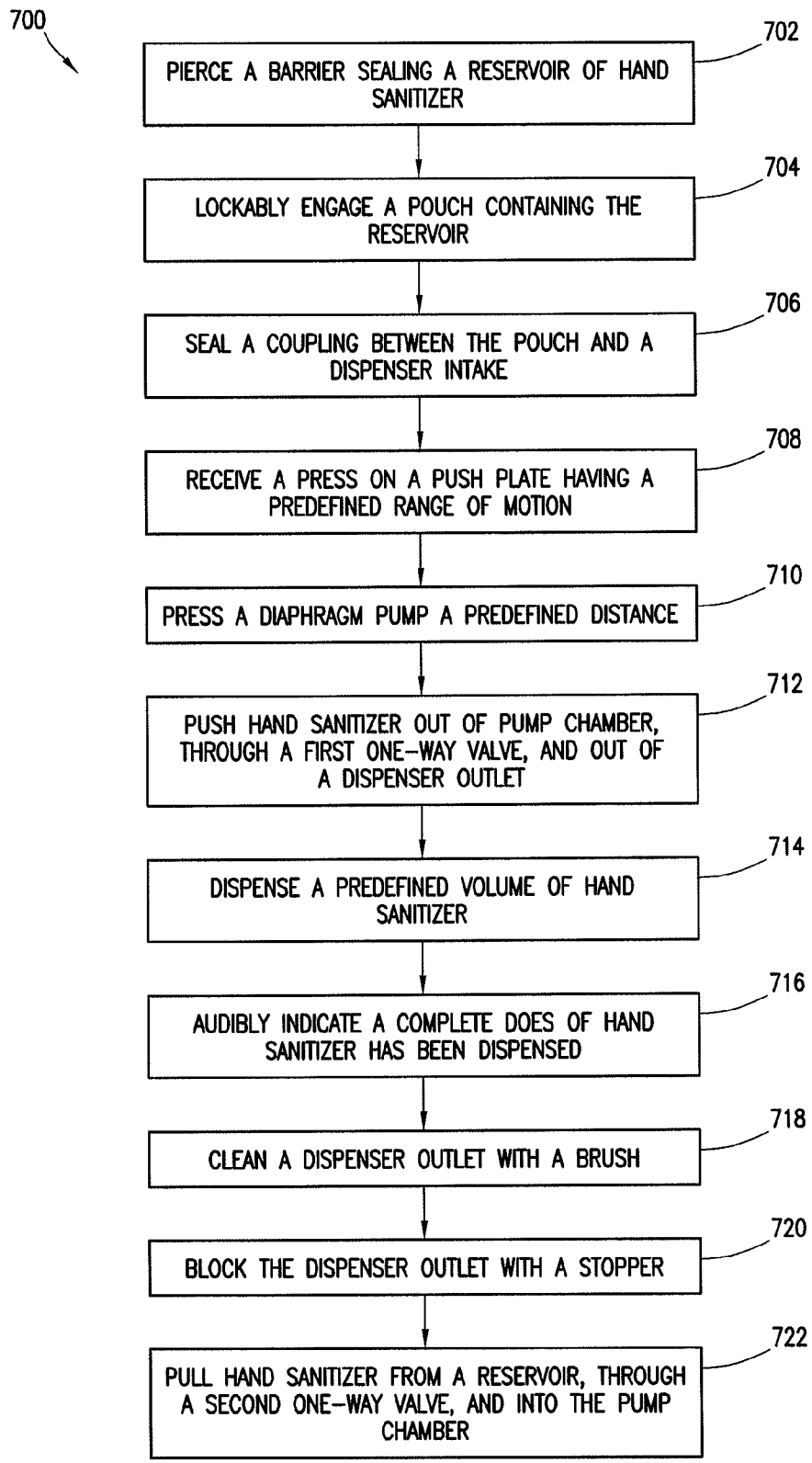
FIG. 7 illustrates a flow chart depicting a method for dispensing hand sanitizer, in accordance with certain embodiments of the present disclosure.

FIG. 7 illustrates a flow chart depicting a method 700 for dispensing hand sanitizer, in accordance with certain embodiments of the present disclosure.

At step 702, method 700 may require piercing a barrier sealing a reservoir of hand sanitizer. For example, in some embodiments, pointed end 236 may pierce seal 240 located on pouch 210, which may include a collapsible plastic bag enclosing a reservoir of hand sanitizer.

At step 704, method 700 may require lockably engaging a pouch containing the reservoir of hand sanitizer. For example, in some embodiments, locking studs 232 may lockably engage with pouch 210 via pouch 210's twist-lock hooks 224.

At step 706, method 700 may require sealing a coupling between the pouch and a dispenser intake. For example, in some embodiments, o-ring 234 may seal the coupling between nozzle 222 of pouch 210 and pump intake 230.

At step 708, method 700 may require receiving a press on push plate 130, which may have a predefined range of motion between a resting position and a pressed position.

At step 710, method 700 may require pressing a diaphragm pump a predefined distance corresponding to the predefined range of motion of push plate 130. For example, in some embodiments, pump actuator 432 may be coupled to push plate 130 and may be configured to make contact with and press diaphragm 450 downward when push plate 130 is pushed downward. Accordingly, in some embodiments, pump actuator 432 may press diaphragm 450 a distance that is approximately the same as or otherwise corresponds to the distance that defines push plate 130's predefined range of motion.

At step 712, method 700 may require pushing hand sanitizer out of pump chamber 472, through a first one-way valve, and out of a dispenser outlet. For example, in some embodiments, when diaphragm 450 is pressed, diaphragm 450 may push sanitizer out of pump chamber 472, through outlet valve 462, and out of the tip of outlet channel 474 and/or the output of outlet valve 462.

At step 714, method 700 may require dispensing a predefined volume of hand sanitizer corresponding to the predefined range of motion of push plate 130. In some embodiments, a predefined range of motion of push plate 130 may cause to pump actuator 432 to press diaphragm 450 a predefined distance, and thus cause diaphragm 450 to displace a predefined volume of sanitizer in pump chamber 472. That predefined volume may in turn be dispensed from dispenser 100.

At step 716, method 700 may require audibly indicating a complete dose of hand sanitizer has been dispensed when the push plate reaches the end of its predefined range of motion. For example, in some embodiments, contact device 530 may be configured to mechanically sense when push plate 130 and lever 535 are fully depressed, and may make a clicking noise when lever 535 is fully depressed.

At step 718, method 700 may require cleaning a dispenser outlet with a brush. For example, in some embodiments, brush 436 may clean the end point of outlet channel 474 and/or the output of outlet valve 462 as push plate 130 transitions from a pressed position to a resting position.

At step 720, method 700 may require blocking the dispenser outlet with a stopper. For example, in some embodiments, stopper 434 may block the end point of outlet channel 474 and/or the output of outlet valve 462 when push plate 130 is in a resting position.

At step 722, method 700 may require pulling hand sanitizer from a reservoir of hand sanitizer, through a second one-way valve, and into the pump chamber. For example, after push plate 130 is pressed and subsequently released, push plate 130 may return to its resting position and diaphragm 450 may recoil to its natural dome-like shape. As diaphragm 450 recoils, it may create a vacuum pressure inside of pump chamber 472. In some embodiments, this vacuum pressure may pull hand sanitizer from the reservoir of hand sanitizer within pouch 210, through intake valve 452, and into pump chamber 472. After step 708 has been completed, method 700 may be repeated to dispense another dose of hand sanitizer.

Although FIG. 7 discloses a particular number of steps to be taken with respect to method 700, method 700 may be executed with greater or lesser steps than those depicted in FIG. 7. For example, in some embodiments, method 700 may be performed without step 722. In addition, although FIG. 7 discloses a certain order of steps to be taken with respect to method 700, the steps comprising method 700 may be completed in any suitable order. For example, in some embodiments, step 708 and step 710 may be completed simultaneously.

Figure 8:
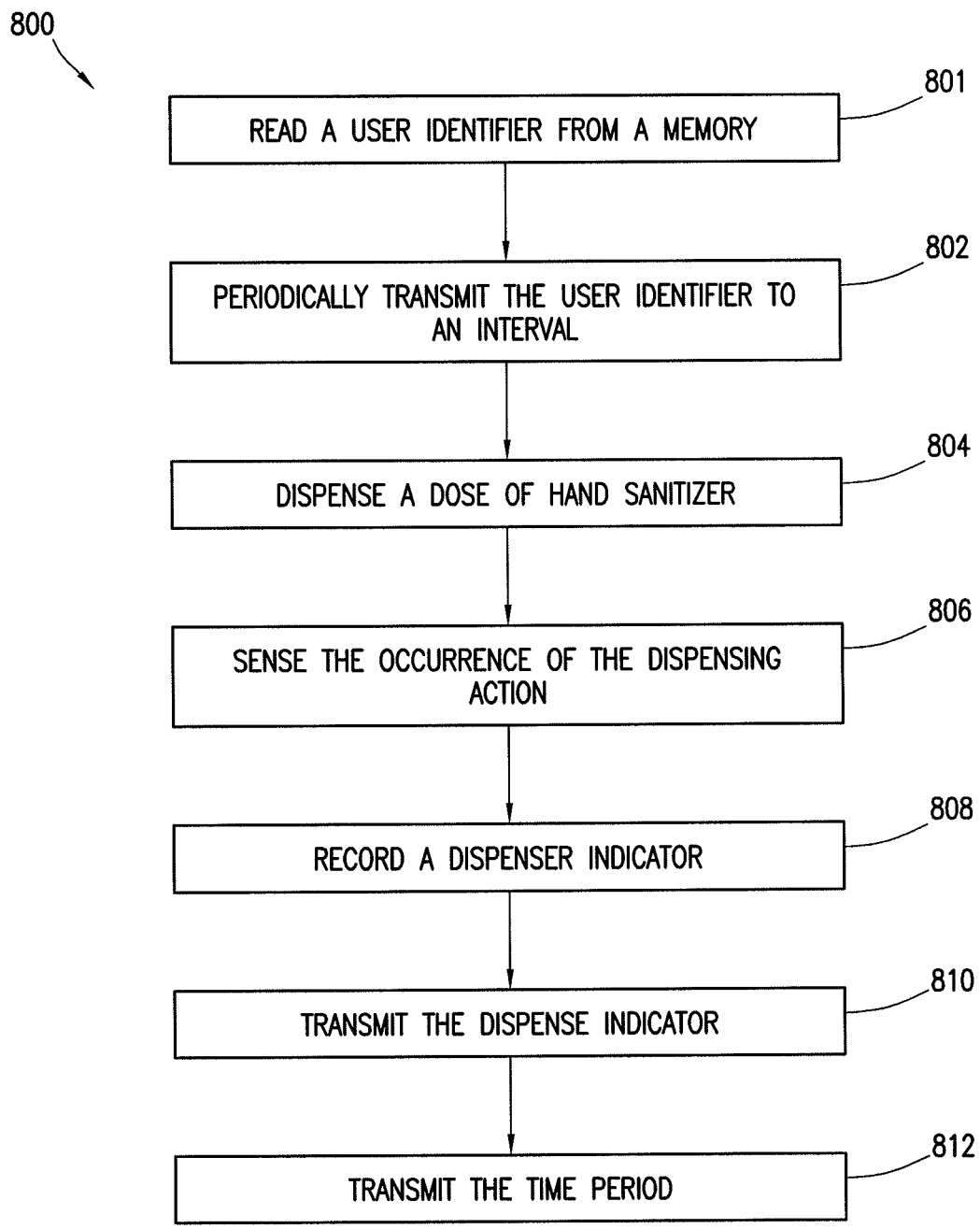
FIG. 8 illustrates a flow chart depicting a method for transmitting information regarding hand sanitization, in accordance with certain embodiments of the present disclosure.

FIG. 8 illustrates a flow chart depicting a method 800 for transmitting information regarding hand sanitization, in accordance with certain embodiments of the present disclosure.

At step 801, method 800 may require reading a user identifier from a memory. For example, in some embodiments, processor 620 may read a user identifier from user identifier memory 610.

At step 802, method 800 may require periodically transmitting a user identifier to a network at an interval. For example, in some embodiments, transceiver 630 may transmit the user identifier to hub 650, which may in turn relay that information to network server 660. In some embodiments, transceiver 630 may be configured according to the ANT protocol and may operate in a low power "sleep mode" in between transmissions. In such embodiments, transceiver 630 may "wake up" at a regular interval to transmit the user identifier to hub 650. The regular interval may be programmed to be a time from approximately five seconds to approximately twenty-five seconds, which may correspond to the approximate time that it may take a user to travel from one location of interest, such as a first patient room in a hospital, to a second location of interest, such as a second patient room in a hospital.

At step 804, method 800 may require dispensing a dose of hand sanitizer. For example, in some embodiments, dispenser 100 may dispense a dose of hand sanitizer when a user presses push plate 130.

At step 806, method 800 may require sensing the occurrence of a dispensing action. For example, in some embodiments, electronic module 520 may include a sensor such as contact switch 525, which may be engaged by a switch actuator when push plate 130 is pressed, and may thus sense the occurrence of a dispensing action that may occur in step 804.

At step 808, method 800 may require recording a dispense indicator corresponding to the dispensing action. In some embodiments, processor 620 may include a timer that may count the time between successful periodic transmissions of the user identifier. When a dispensing action is sensed at step 806, processor 620 may record a dispense indicator, which may include a time stamp corresponding to the time since the previous successful periodic transmission of the user identifier.

At step 810, method 800 may require transmitting the dispense indicator to the network. At step 812, method 800 may require transmitting a time period with the dispense indicator. In some embodiments, transceiver 630 may be programmed to transmit the dispense indicator and the time period with the user identifier to hub 650 at the next periodic transmission of the user identifier following the dispensing action. In some embodiments, the dispense indicator may include a time stamp that may be the time from the previous successful periodic transmission of the user identifier to the sensing of the dispensing action. In some embodiments, the time period may be an amount of time from the previous successful periodic transmission of the user identifier to the next periodic transmission of the user identifier following the dispensing action. When hub 650 receives the dispense indicator, the time period, and the user identifier, hub 650 may relay that information, along with a location identifier corresponding to the physical location of hub 650, to network server 660. Accordingly, network server 660 may receive information regarding where a dispenser user traveled, when they traveled there, as well as information allowing network server 660 to determine when that user sanitized their hands.

Although FIG. 8 discloses a particular number of steps to be taken with respect to method 800, method 800 may be executed with greater or lesser steps than those depicted in FIG. 8. For example, in some embodiments, method 800 may be completed without step 802. In addition, although FIG. 8 discloses a certain order of steps to be take with respect to method 800, the steps comprising method 800 may be completed in any suitable order. For example, in some embodiments, step 804 and step 806 may be completed simultaneously.

For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory; as well as communications media such wires, optical fibers, and other electromagnetic and/or optical carriers; and/or any combination of the foregoing. The following examples pertain to further embodiments. Specifics in the examples may be used anywhere in one or more embodiments described above or herein.

Although the present disclosure has been described in detail, it should be understood that various changes, substitutions, and alterations can be made hereto without departing from the spirit and the scope of the disclosure as defined by the appended claims.

What is claimed is:

1. An electronic module comprising:
a sensor configured to detect a dispensing action;
a processor configured to:
record a dispense indicator when the sensor detects a dispensing action; and
read a user identifier from a user identifier memory configured to interchangeably operate in conjunction with a plurality of sanitizer dispensers; and
a transceiver configured to:
periodically transmit the user identifier to a network at an interval of time; and
transmit the dispense indicator and a time period to the network with the user identifier at a next periodic transmission of the user identifier following the dispensing action;
wherein the time period is a time from a previous periodic transmission of the user identifier to the next periodic transmission of the user identifier following the dispensing action.

2. The electronic module of claim 1, wherein the electronic module is configured to be interchangeably placed within one of the plurality of sanitizer dispensers.

3. The electronic module of claim 1, wherein the memory is located on an interchangeable memory card.

4. The electronic module of claim 1, wherein the interval is a time from approximately one second to approximately sixty seconds.

5. The electronic module of claim 1, wherein the dispense indicator comprises a time stamp comprising a time from a previous periodic transmission of the user identifier to the dispensing action.

6. The electronic module of claim 1, wherein:
the transceiver is further configured to:
receive a location identifier from a location transmitter; and
transmit a location identifier to a network; and
the processor is further configured to record the location identifier.

7. The electronic module of claim 1, wherein the transceiver is configured according to the ANT protocol.

8. A method, comprising:
reading a user identifier from a user identifier memory;
periodically transmitting a user identifier to a network at an interval;
sensing an occurrence of a dispensing action;
recording a dispense indicator corresponding to the dispensing action;
transmitting the dispense indicator to the network; and
transmitting a time period with the dispense indicator;
wherein the dispense indicator and the time period are transmitted with a next periodic transmission of the user identifier following the sensing of the occurrence of the dispensing action; and
wherein the time period is a time from a previous periodic transmission of the user identifier to the next periodic transmission of the user identifier following the dispensing action.

9. The method of claim 8, further comprising dispensing a dose of sanitizer.

10. The method of claim 8, wherein the user identifier memory is located on an interchangeable memory card.

11. The method of claim 8, wherein the interval is a time from approximately one second to approximately sixty seconds.

12. The method of claim 8, wherein the dispense indicator comprises a time stamp comprising a time from a previous periodic transmission of the user identifier to the occurrence of the dispensing action.

13. The method of claim 8, further comprising:
receiving a location identifier from a location transmitter; and
transmitting the location identifier to the network with periodic transmissions of the user identifier.

14. The method of claim 8, wherein the transmission of the user identifier and the transmission of the dispense indicator occur in compliance with the ANT protocol.

15. A sanitizer dispenser comprising:
a sanitizer pump; and
an electronic module comprising:
a sensor configured to detect a dispensing action;
a processor configured to:
record a dispense indicator when the sensor detects a dispensing action; and
read a user identifier from a user identifier memory configured to interchangeably operate in conjunction with a plurality of sanitizer dispensers; and
a transceiver configured to:
periodically transmit the user identifier to a network at an interval of time; and
transmit the dispense indicator and a time period to the network with the user identifier at a next periodic transmission of the user identifier following the dispensing action;
wherein the time period is a time from a previous periodic transmission of the user identifier to the next periodic transmission of the user identifier following the dispensing action.

16. The sanitizer dispenser of claim 15, wherein the memory is located on an interchangeable memory card.

* * * * *